(12) United States Patent
Hellwig et al.

(10) Patent No.: US 7,869,851 B2
(45) Date of Patent: Jan. 11, 2011

(54) SYSTEM AND METHOD FOR DETERMINING INSULIN BOLUS QUANTITIES

(75) Inventors: Robert Hellwig, Borken (DE); Stefan Weinert, Pendleton, IN (US)

(73) Assignees: Roche Diagnostics Operations, Inc., Indianapolis, IN (US); Roche Diagnostics International AG (CH)

( * ) Notice: Subject to any disclaimer, the term of this patent is extended or adjusted under 35 U.S.C. 154(b) by 1715 days.

(21) Appl. No.: 11/022,100

(22) Filed: Dec. 23, 2004

(65) Prior Publication Data
US 2006/0137695 A1 Jun. 29, 2006

(51) Int. Cl.
A61B 5/00 (2006.01)

(52) U.S. Cl. ..................................... 600/345

(58) Field of Classification Search ......... 600/345–366, 600/309, 300
See application file for complete search history.

(56) References Cited

U.S. PATENT DOCUMENTS

| | | | |
|---|---|---|---|
| 5,713,856 A | 2/1998 | Eggers et al. | |
| 5,822,715 A | 10/1998 | Worthington et al. | |
| 6,352,505 B1 | 3/2002 | Bortz | |
| 6,379,301 B1 | 4/2002 | Worthington et al. | |
| 6,427,088 B1 | 7/2002 | Bowman, IV et al. | |
| 6,461,331 B1 | 10/2002 | Van Antwerp | |
| 6,471,675 B1 | 10/2002 | Rogers et al. | |
| 6,551,276 B1 * | 4/2003 | Mann et al. | 604/131 |
| 6,554,798 B1 | 4/2003 | Mann et al. | |
| 6,558,351 B1 | 5/2003 | Steil et al. | |
| 6,562,001 B2 | 5/2003 | Lebel et al. | |
| 6,571,128 B2 | 5/2003 | Lebel et al. | |
| 6,577,899 B2 | 6/2003 | Lebel et al. | |
| 6,579,280 B1 | 6/2003 | Kovach et al. | |
| 6,585,644 B2 | 7/2003 | Lebel et al. | |
| 6,635,049 B1 | 10/2003 | Robinson et al. | |
| 6,641,533 B2 | 11/2003 | Causey, III et al. | |
| 6,648,821 B2 | 11/2003 | Lebel et al. | |
| 6,659,948 B2 | 12/2003 | Lebel et al. | |
| 6,687,546 B2 | 2/2004 | Lebel et al. | |

(Continued)

FOREIGN PATENT DOCUMENTS

EP 1759726 A2 3/2007

OTHER PUBLICATIONS

Insulin Aspart (B28 APS-Insulin): A Fast-Acting Analog of Human Insulin, Diabetes Care, vol. 22, No. 9, Sep. 1999.

*Primary Examiner*—Charles A Marmor, II
*Assistant Examiner*—Navin Natnithithadha
(74) *Attorney, Agent, or Firm*—Barnes & Thornburg LLP

(57) ABSTRACT

A method of computing an insulin bolus quantity when a measured glucose value in a current time interval exceeds a target glucose value for the current time interval and when a time duration of glucose lowering action of the bolus to be administered spans the current and a number of the next adjacent time intervals, may comprise determining a corresponding number of percentages of insulin action of the recommended bolus quantity that will each be used lowering the glucose level during a respective one of the number of time intervals, and computing the recommended bolus quantity as a function of the measured glucose value, the target blood glucose level for a last one of the number of next adjacent time intervals, the insulin sensitivities for the current and each of the number of next adjacent time intervals, and the corresponding number of percentages.

26 Claims, 5 Drawing Sheets

U.S. PATENT DOCUMENTS

| | | |
|---|---|---|
| 6,690,280 B2 | 2/2004 | Citrenbaum et al. |
| 6,691,043 B2 | 2/2004 | Ribeiro, Jr. |
| 6,733,471 B1 | 5/2004 | Ericson et al. |
| 6,740,072 B2 | 5/2004 | Starkweather et al. |
| 6,740,075 B2 | 5/2004 | Lebel et al. |
| 6,744,350 B2 | 6/2004 | Blomquist |
| 7,291,107 B2 * | 11/2007 | Hellwig et al. ............... 600/365 |
| 7,404,796 B2 * | 7/2008 | Ginsberg .................... 600/365 |
| 7,553,281 B2 * | 6/2009 | Hellwig et al. ............... 600/365 |
| 2002/0002326 A1 | 1/2002 | Causey, III et al. |
| 2002/0087120 A1 | 7/2002 | Rogers et al. |
| 2002/0107476 A1 | 8/2002 | Mann et al. |
| 2002/0193679 A1 | 12/2002 | Malave et al. |
| 2003/0028089 A1 * | 2/2003 | Galley et al. ................ 600/365 |
| 2003/0032867 A1 | 2/2003 | Crothall et al. |
| 2003/0048185 A1 | 3/2003 | Citrenbaum et al. |
| 2003/0055570 A1 | 3/2003 | Ribeiro, Jr. |
| 2003/0060765 A1 | 3/2003 | Campbell et al. |
| 2003/0069614 A1 | 4/2003 | Bowman, IV et al. |
| 2003/0114836 A1 | 6/2003 | Estes et al. |
| 2003/0130616 A1 | 7/2003 | Steil et al. |
| 2003/0176933 A1 | 9/2003 | Lebel et al. |
| 2003/0181851 A1 | 9/2003 | Mann et al. |
| 2003/0181852 A1 | 9/2003 | Mann et al. |
| 2003/0187525 A1 | 10/2003 | Mann et al. |
| 2003/0191431 A1 | 10/2003 | Mann et al. |
| 2003/0199854 A1 | 10/2003 | Kovach et al. |
| 2003/0204274 A1 | 10/2003 | Ullestad et al. |
| 2003/0212364 A1 | 11/2003 | Mann et al. |
| 2004/0068230 A1 | 4/2004 | Estes et al. |
| 2004/0073095 A1 | 4/2004 | Causey, III et al. |
| 2004/0167464 A1 | 8/2004 | Ireland et al. |
| 2004/0220517 A1 | 11/2004 | Starkweather et al. |
| 2005/0203360 A1 * | 9/2005 | Brauker et al. ............... 600/345 |
| 2006/0047192 A1 * | 3/2006 | Hellwig et al. ............... 600/365 |
| 2007/0060869 A1 | 3/2007 | Tolle et al. |
| 2007/0060870 A1 | 3/2007 | Tolle et al. |
| 2008/0058628 A1 * | 3/2008 | Hellwig et al. ............... 600/365 |

* cited by examiner

US 7,869,851 B2

SYSTEM AND METHOD FOR DETERMINING INSULIN BOLUS QUANTITIES

FIELD OF THE INVENTION

The present invention relates generally to techniques for managing glucose levels in diabetic individuals, and more specifically to systems for determining and recommending insulin administration as a way of managing glucose levels.

BACKGROUND

A number of handheld and other systems for managing diabetes care currently exist. Many such systems provide for the partitioning of an extended time period, e.g., one or more days, into a number of adjacent time intervals. Within each time interval, a specific glucose target and a specific insulin sensitivity value, e.g., in units of mg/dl per international unit (IU) of insulin, may be established. It is desirable with such systems to provide for accurate determination and recommendation of additive correction insulin bolusing, regardless of when such bolusing may occur relative to adjacent time intervals, to thereby closely track and satisfy the user's insulin needs.

SUMMARY

The present invention may comprise one or more of the features recited in the attached claims, and/or one or more of the following features and combinations thereof. A diabetes care system may have a number of adjacent time intervals each defining an associated target glucose value and an insulin sensitivity value. A method of computing a recommended insulin bolus quantity when a measured glucose value in a current time interval exceeds the target glucose value for the current time interval and when a time duration of glucose lowering action of the recommended insulin bolus quantity to be administered spans the current time interval and a next adjacent time interval, may comprise determining a corresponding number of percentages each corresponding to a percentage of insulin action of the recommended bolus quantity that will be used lowering the glucose level during a respective one of the number of time intervals between the current time interval and the number of next adjacent time intervals. The recommended bolus quantity may be computed as a function of the measured glucose value, the target blood glucose level for a last one of the number of next adjacent time intervals, the insulin sensitivities for the current and each of the number of next adjacent time intervals, and the corresponding number of percentages.

The number of next adjacent time intervals may be one, and the step of determining a corresponding number of percentages may include determining a first percentage corresponding to a percentage of insulin action of the recommended bolus quantity that will be used lowering the glucose level during the current time interval, and determining a second percentage corresponding to a percentage of insulin action of the recommended bolus quantity that will be used lowering the glucose level during the next time interval. The computing may then comprise computing the recommended bolus quantity as a function of the measured glucose value, the target blood glucose level for the next adjacent time interval, the insulin sensitivities for the current and next adjacent time intervals, and the first and second percentages.

The step of determining a first percentage may include determining the first percentage as a function of at least a current time in the current time interval at which the measured bolus value was measured, a beginning time of the next adjacent time interval and the time duration of glucose lowering action of the subsequently administered recommended insulin bolus quantity. The method may further include the step of computing a current interval bolus activity time as a difference between the beginning time of the next adjacent time interval and the current time. The step of determining a first percentage may then include determining the first percentage as a function of the current interval bolus activity time and the time duration of glucose lowering action of the subsequently administered recommended insulin bolus quantity. The step of determining a first percentage may include extracting the first percentage value from a table populated with first percentage values as functions of current interval bolus activity time values and time duration values of glucose lowering action of the subsequently administered recommended insulin bolus quantity. The step of determining a second percentage may include computing the second percentage as a difference between one hundred percent and the first percentage.

Alternatively, the step of determining a second percentage may include determining the second percentage as a function of at least a current time in the current time interval at which the measured bolus value was measured, a beginning time of the next adjacent time interval and the time duration of glucose lowering action of the subsequently administered recommended insulin bolus quantity. In this embodiment, the method may further include the step of computing a next interval bolus activity time as a difference between the time duration of glucose lowering action of the subsequently administered recommended insulin bolus quantity and a current interval bolus activity time corresponding to a difference between the beginning time of the next adjacent time interval and the current time. The step of determining a second percentage may then include determining the second percentage as a function of the next interval bolus activity time and the time duration of glucose lowering action of the subsequently administered recommended insulin bolus quantity. The step of determining a second percentage may include extracting the second percentage value from a table populated with second percentage values as functions of next interval bolus activity time values and time duration values of glucose lowering action of the subsequently administered recommended insulin bolus quantity. The step of determining a first percentage may include computing the first percentage as a difference between one hundred percent and the second percentage.

In either case, the method may further including the step of executing both determining steps and the computing step only if the time duration of glucose lowering action of the subsequently administered recommended insulin bolus quantity extends into the next adjacent time interval by a predefined time amount.

A method of computing a recommended insulin bolus quantity when a measured glucose value in a current one of the time intervals exceeds the target glucose value for the current time interval, may comprise determining whether a time duration of glucose lowering action of the recommended insulin bolus quantity to be administered spans the current time interval and at least the next adjacent time interval. The method may further include computing the recommended bolus quantity as a function of the measured glucose value, the target glucose value for the current time interval and the insulin sensitivity value for the current time interval only if the time duration of glucose lowering action of the subsequently administered recommended insulin bolus quantity is confined to the current time interval. The method may further include a number of additional steps if the time duration of the glucose lowering action of the subsequently administered recommended insulin bolus quantity otherwise spans the current and at least the next adjacent time interval. For example, the method may include determining a first percentage corresponding to a percentage of insulin action of the recommended bolus quantity that will be used lowering the glucose level during the current time interval. The method may further include determining a second percentage corresponding to a percentage of insulin action of the recommended bolus quantity that will be used lowering the glucose level during the next time interval. The method may further include computing the recommended bolus quantity as a function of the measured glucose value, the target blood glucose level for the next adjacent time interval, the insulin sensitivities for the current and next adjacent time intervals, and the first and second percentages.

A method of computing a recommended insulin bolus quantity when a measured glucose value in a current one of the time intervals exceeds the target glucose value for the current time interval and when a time duration of glucose lowering action of the subsequently administered recommended insulin bolus quantity spans the current time interval and a next adjacent time interval, may comprise determining a first difference as a difference between the target glucose value for the current time interval and the target glucose value for the next adjacent time interval. The method may further include determining a second difference as a difference between the insulin sensitivity value for the current time interval and the insulin sensitivity value for the next adjacent time interval. The method may further include computing the recommended bolus quantity as a function of the measured glucose value, the target glucose value for the current time interval and the insulin sensitivity value for the current time interval only if the first difference is less than a first threshold value and the second difference is less than a second threshold value. The method may further including a number of additional steps if either of the first difference exceeds the first threshold value and the second difference exceeds the second threshold value. For example, the method may include determining a first percentage corresponding to a percentage of insulin action of the recommended bolus quantity that will be used lowering the glucose level during the current time interval. The method may further include determining a second percentage corresponding to a percentage of insulin action of the recommended bolus quantity that will be used lowering the glucose level during the next time interval. The method may further include computing the recommended bolus quantity as a function of the measured glucose value, the target blood glucose level for the next adjacent time interval, the insulin sensitivities for the current and next adjacent time intervals, and the first and second percentages.

These and other features of the present invention will become more apparent from the following description of the illustrative embodiments.

DESCRIPTION OF THE ILLUSTRATIVE EMBODIMENTS

For the purposes of promoting an understanding of the principles of the invention, reference will now be made to a number of illustrative embodiments shown in the attached drawings and specific language will be used to describe the same.

Figure 1:
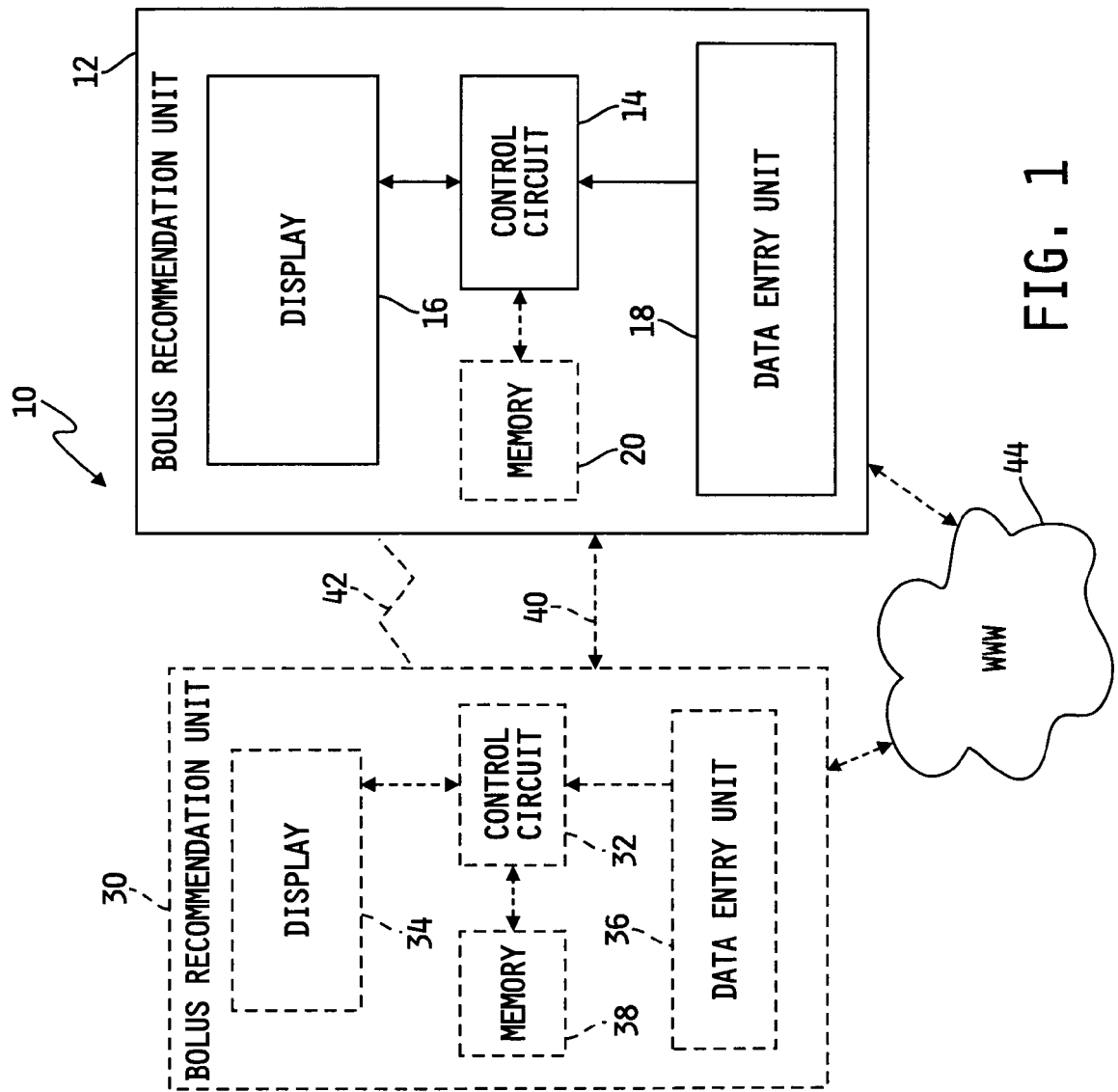
FIG. 1 is a block diagram of one illustrative embodiment of an insulin bolus recommendation system.

Referring now to FIG. 1, a block diagram of one illustrative embodiment of an insulin bolus recommendation system 10 is shown. In the illustrated embodiment, the insulin bolus recommendation system 10 includes a bolus recommendation unit 12 having at least a control circuit 14 electrically connected to a visual display unit 16 and also to a data entry unit 18. The control circuit 14 may illustratively be a conventional, microprocessor-based control computer capable of executing one or more software algorithms, although the control circuit 14 may alternatively be any single one or collection of electronic circuits capable of operation as described hereinafter. In some embodiments, the control circuit 14 may be electrically connected to a conventional memory unit 20 as shown in phantom. The visual display unit 16 may be or include any conventional display screen including, but not limited to, a cathode ray tube (CRT) display, a liquid crystal display (LCD), a plasma display, a single or multicolor monitor, a touch-sensitive data entry screen, or the like. The data entry unit 18 may be or include any conventional data input device including, but not limited to, a key board or key pad, a mouse or similar point-and-click device, one or more coded or non-coded, touch-sensitive switches associated with the display unit 16, a voice-activated data input device, or the like.

The insulin bolus recommendation system 10 may, in some embodiments, further include an additional bolus recommendation unit 30 as shown in phantom in FIG. 1. The unit 30 may include a control circuit 32 electrically connected to a visual display unit 34 and also to a data entry unit 36, wherein the control circuit 32, display unit 34 and data entry unit 36 may be provided in any of the forms described hereinabove with respect to the bolus recommendation unit 12. The control circuit 32 may further be electrically connected to a conventional memory unit 38. In this embodiment, the bolus recommendation unit 12 and the bolus recommendation unit 30 may be each configured to share information via a wired connection 40 including one or more signal paths physically connecting the two units, via a wireless signal path 42 such as a radio signal or cellular telephone link, and/or via the world-wide-web (WWW) 44, each using conventional technology.

The insulin bolus recommendation system 10 is configured to determine and recommend administration of one or more specific insulin bolus quantities into the blood stream of a user of the system 10 according to an insulin bolus recommendation protocol embodied in the system 10 as one or more executable software algorithms. The physical structure of the insulin bolus recommendation system 10 for executing such software algorithms and for communicating useful information between the system 10 and the user may take various forms. In one illustrative embodiment, for example, the bolus recommendation system 10 includes only the bolus recommendation unit 12 embodied as a conventional personal computer (PC), laptop or notebook computer, personal data assistant (PDA) or the like, or as a hand-held, lap top or desk top application-specific bolus recommendation unit. In any of these cases, the bolus recommendation unit 12 includes the memory unit 20 having the number of executable software algorithms stored therein, and the control circuit 14 is operable to execute these software algorithms to determine and recommend one or more injections of specific insulin bolus quantities into the blood stream of the user according to an insulin bolus recommendation protocol as will be described in detail hereinafter. In this embodiment, the display unit 16 is controlled by the control circuit 14 under the direction of the software algorithms to communicate information to the user and to prompt the user for information that the user may enter via the data entry unit 18.

In another illustrative embodiment, the insulin bolus recommendation system 10 includes the bolus recommendation unit 12 and the bolus recommendation unit 30. As one example of this embodiment, the bolus recommendation unit 12 may be a PDA or application-specific bolus recommendation unit as described hereinabove, and the bolus recommendation unit 30 may be a PC, laptop or notebook computer. In this embodiment, the unit 12 may communicate with the unit 30 either via the wireless interface 42 or via the wired interface 40 that may be electrically connected to a PDA or application-specific bolus recommendation unit cradle configured to receive the unit 12 and electrically connect the unit 12 in data communications with the unit 30. In this example, the memory units 20 and 38 of the units 12 and 30 respectively may each have the number of software algorithms stored therein, and the user may use the bolus recommendation unit 12 as a mobile insulin bolus recommendation unit and/or use the bolus recommendation unit 30 as a stationary insulin bolus recommendation unit. In this case, the user will maintain the databases of each unit 12 and 30 current by periodically synchronizing the databases of both units 12 and 30 via the wired or wireless interface 40 or 42 respectively.

As another example of the embodiment of the insulin bolus recommendation system 10 that includes the bolus recommendation unit 12 and the bolus recommendation unit 30, the bolus recommendation unit 12 may be a PDA, PC, laptop or notebook computer, cellular telephone or any other unit or device capable of accessing the WWW 44. In this example, the bolus recommendation unit 12 need not have the number of software algorithms stored in the memory unit 20, and need not include the memory unit 20 at all. The bolus recommendation unit 30 may, in the example, be a remote computer or conventional web server also configured to access the WWW 44 and having the number of software algorithms stored in the memory unit 38. The control circuit 32 of the remote computer or web server 30 is operable in this example to execute the number of software algorithms based on information provided over the WWW 44 by the user via the bolus recommendation unit 12. In this particular embodiment, the user and/or a health care provider may access a web page or web site controlled by the bolus recommendation unit 30 and provide the initial operating parameters and/or limits for the insulin bolus recommendation protocol to the control circuit 32. The user may then and thereafter access the web page or web site and enter current blood glucose information, and the control circuit 32 may then determine and recommend via the web page or web site one or more injections of specific insulin bolus quantities into the users blood stream, based on the current blood glucose information according to the insulin bolus recommendation protocol that will be described in detail hereinafter.

In this particular embodiment, the insulin bolus recommendation software algorithms thus reside in the remote computer or web server 30, and in this regard the bolus recommendation unit 12 need only include sufficient hardware so as to be capable of providing current blood glucose information to the web page or web site and of viewing the recommendation results produced on the web page or web site by the remote computer or web server 30. As a practical matter, though, it may further be desirable in this embodiment to provide the bolus recommendation unit 12 with the memory unit 20 and store the number of bolus recommendation software algorithms therein so that the bolus recommendation unit 12 may independently execute these software algorithms when it may not be possible or practicable to access the WWW 44 and/or the appropriate web page or web site. It will further be desirable in such an embodiment to provide for the synchronization of the remote and/or web-based database with the database stored in the memory unit 20 of the bolus recommendation unit 12.

It will be appreciated that the insulin bolus recommendation system 10 may be configured to cooperate with a glucose meter or other automatic blood glucose determination unit and/or an insulin pump or other automatic insulin dosing or administering unit. In embodiments wherein a glucose meter or other automatic blood glucose determination unit is included with the insulin bolus recommendation system 10, the control computer 14 may be configured to prompt such a unit, using conventional techniques, to automatically produce current blood glucose information which the system 10 may then use, as will be described in detail hereinafter, to determine and recommend administering one more insulin bolus quantities. In embodiments wherein an insulin pump or other automatic insulin dosing unit is included with the insulin bolus recommendation system 10, the control computer 14 may be configured to prompt such a unit, using conventional techniques, to automatically administer recommended insulin bolus quantities to the user.

As described hereinabove, the insulin bolus recommendation system 10 illustrated in FIG. 1 is operable to execute a number of software algorithms for determining and recommending administering of one or more of specific insulin bolus quantities into the blood stream of the user according to an insulin bolus recommendation protocol. The insulin bolus protocol, as it relates to the present disclosure, provides for the partitioning of an extended time period, e.g., one or more days, into a number of adjacent time intervals. With any such time interval, a specific target glucose level and a specific insulin sensitivity value may be defined. The target glucose level for any time interval corresponds to a constant glucose value within that time interval that the user would like to maintain. One example target glucose level may be 120 mg/dl, although the various target glucose levels defined in the number of time intervals may take on other values. The insulin sensitivity value for any time interval corresponds to the decrease glucose, e.g., in mg/dl per unit of infused insulin. One example insulin sensitivity value may be 30 mg/dl/IU, although other insulin sensitivity values may alternatively be used. Details relating to example software algorithms suitable for execution by the system 10 for carrying out such an insulin bolus protocol are described in U.S. patent application Ser. No. 10/927,614, which is assigned to the assignee of the subject invention, and the disclosure of which is incorporated herein by reference. It should be understood, however, that the system 10 may alternatively or additionally be programmed to execute other conventional software algorithms for carrying out such an insulin bolus protocol.

Figure 2:
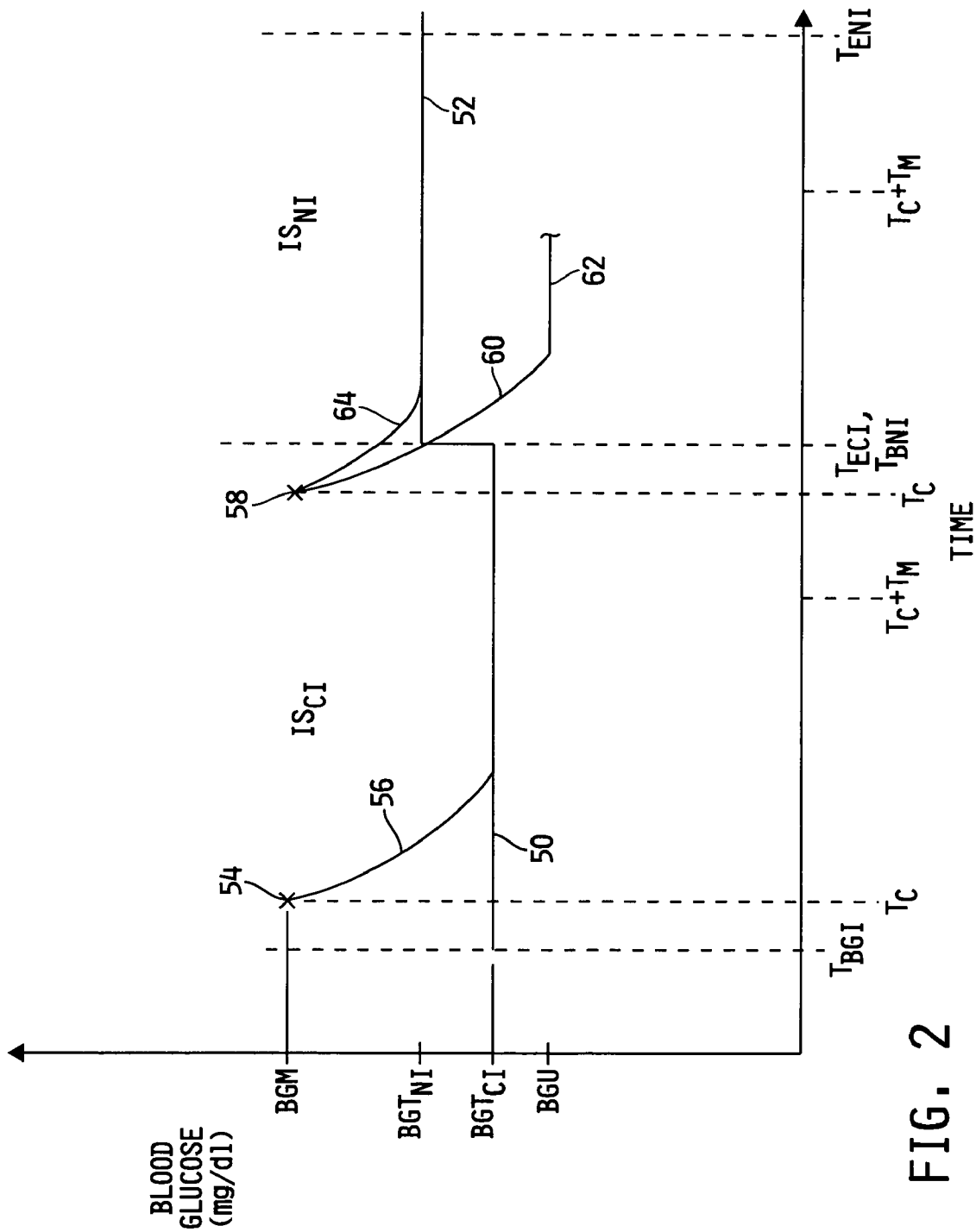
FIG. 2 is a plot of blood glucose vs. time illustrating a number of examples of insulin bolus administration relative to a current and next adjacent time interval.

Referring now to FIG. 2, a plot of blood glucose vs. time is shown illustrating two time intervals according to the above-described insulin bolus protocol. A current time interval begins at a "begin current interval" time, $T_{BCI}$, and ends at a subsequent "end current interval" time, $T_{ECI}$. The target blood glucose 50 defined during the current interval is designated $BGT_{CI}$, and the insulin sensitivity defined during the current interval is designated $IS_{CI}$. A next adjacent time interval begins at a "begin next interval" time, $T_{BNI}$, which coincides with the "end current interval" time, $T_{ECI}$, and ends at a subsequent "end next interval" time, $T_{ENI}$. The target blood glucose 52 defined during the next adjacent interval is designated $BGT_{NI}$, and the insulin sensitivity defined during the next adjacent interval is designated $IS_{NI}$.

The user of the system 10 may, at any time, obtain a measurement of the user's glucose level via one or more conventional techniques. If the current measurement of the user's glucose level exceeds the target blood glucose level for the current interval, $BGT_{CI}$, conventional bolus recommendation systems are typically operable to compute a recommended correction insulin bolus, CB, according to the equation:

$$CB = (BGM - BGT_{CI})/IS_{CI}, \quad (1)$$

where BGM is the blood glucose level measured at the current time, $T_C$. The user then administers the recommended correction insulin bolus near the time $T_C$, and the administered insulin bolus functions in a known manner to lower the glucose level over a time period $T_M$, where $T_M$ is defined for purposes of this document as the duration of the glucose lowering action of an administered insulin bolus.

Referring again to FIG. 2, the foregoing scenario is illustrated in the current interval where a blood glucose value 54 is measured at the current time, $T_C$. With a correction bolus, CB, computed as just described administered near $T_C$, the blood glucose decreases 56 over time in this example to the target glucose value 50, which corresponds to the target blood glucose value for the current interval, $BGT_{CI}$, and remains at $BGT_{CI}$ for the duration $T_M$. Using a numerical example, assume that the measured blood glucose value, BGM, corresponding to point 54, is 200 mg/dl, the target blood glucose value during the current interval, $BGT_{CI}$, is 120 mg/dl, and the insulin sensitivity during the current interval, $IS_{CI}$, is 30 mg/dl/IU. Substituting these numbers into the conventional correction bolus equation described above yields (200 mg/dl−120 mg/dl)/30 mg/dl/IU=2.667, or approximately 2.7 IU. Thus, during the current interval, it takes approximately 2.7 IU of insulin to lower the user's glucose level from 200 mg/dl to the target 120 mg/dl.

As illustrated in the example just given, the conventional correction bolus equation works well as long as the correction bolus is administered sufficiently early in the current time interval so that the duration of the glucose lowering action of the administered insulin bolus, $T_M$, is confined to the current interval. However, using the conventional correction bolus equation as a basis for computing and administering a correction bolus at a current time, $T_C$, that occurs later in the current time interval, so that the duration of the glucose lowering action of the administered bolus, $T_M$, spans the current and next adjacent time intervals, may yield undesirable results. For example, consider the case where a blood glucose value 58 is measured at the now current time, $T_C$, near the end, $T_{ECI}$, of the current time interval (corresponding to the beginning time, $T_{BNI}$, of the next adjacent time interval). With a correction bolus, CB, computed using the conventional equation described above and administered near $T_C$, the blood glucose decreases over time 60, in this example, into the next adjacent time interval and to a glucose level 62 that may be significantly below the target glucose value 52 of the next adjacent time interval. Using another numerical example, assume that the measured blood glucose value, BGM, corresponding to point 58, is again 200 mg/dl, the target blood glucose value during the current interval, $BGT_{CI}$, is again 120 mg/dl, the insulin sensitivity during the current interval, $IS_{CI}$, is again 30 mg/dl/IU, the target blood glucose value during the next adjacent time interval, $BGT_{NI}$, is 150 mg/dl and the insulin sensitivity during the next adjacent time interval, $IS_{NI}$, is 40 mg/dl/IU. Since $T_C$ is still in the current time interval, the conventional correction bolus equation described above again yields (200 mg/dl−20 mg/dl)/30 mg/dl/IU=2.667, or approximately 2.7 IU. However, suppose that $T_C$ in this example is within one minute of $T_{BNI}$. If the user had waited another minute to take the blood glucose measurement, so that the next adjacent time interval was now the current time interval, the conventional correction bolus equation described above would have yielded (200 mg/dl−150 mg/dl)/40 mg/dl/IU=1.25, or approximately 1.3 IU. Administering a 2.7 IU insulin bolus at or near $T_C$ in this example, thus results in unnecessary insulin in the amount of 1.4 IU which, at an insulin sensitivity, $IS_{NI}$, of 40 mg/dl/IU results in a blood glucose undershoot 62 of (40 mg/dl/IU*1.4 IU)=56 mg/dl below the blood glucose target $BGT_{NI}$, corresponding to a final glucose reduction from 200 mg/dl at point 58 to 94 mg/dl at 62.

One effective technique for improving the accuracy of the correction bolus determination in cases where the time duration, $T_M$, of the glucose lowering action of the administered insulin bolus spans the current and the next time interval is to take into account the time-dependent nature of the target glucose level and of the insulin sensitivity. For example, if h(τ) is the relative amount of insulin activity used up for a bolus of insulin (of a given type) administered at τ=0. At $\tau \geq T_M$, h(τ)=1. If IS(T) is then the insulin sensitivity as a function of time, then a bolus of insulin given at an arbitrary time $T=T_A$ has the following impulse response:

$$H(T, T_A) = \int_0^{T-T_A} \dot{h}(\tau) \cdot IS(T_A + \tau) \cdot d\tau, \quad (2)$$

where $\dot{h}(\tau)$ is the time derivative of h(τ).

If D(T) is the time-dependent insulin bolus infusion rate function, the glucose drop at a give time relative to $BG_{-\infty} = BG(T \to -\infty)$ yields:

$$\Delta BG(T) = \int_{-\infty}^{T} D(T_A) \cdot \int_0^{T-T_A} \dot{h}(\tau) \cdot IS(T_A + \tau) \cdot d\tau \cdot dT_A. \quad (3)$$

To calculate at the current time $T=T_C$ the blood glucose drop $\Delta BG_{pb}$ that will happen in the future caused by the already administered past insulin boli, the following equation is used:

$$\Delta BG_{pb}(T_C) = \int_{T_C-T_M}^{T_C} D(T_A) \cdot \int_{T_C-T_A}^{T_C-T_A+T_M} \dot{h}(\tau) \cdot IS(T_A + \tau) \cdot d\tau \cdot dT_A. \quad (4)$$

To calculate a correction bolus amount, CB, to be given soon after $T=T_C$ with a bolus infusion duration that is negligible against $T_M$, the following equation is used:

$$CB = (\Delta BG_{needed} - \Delta BG_{pb}(T_C)) \bigg/ \int_0^{T_M} h(\tau) \cdot IS(T_C + \tau) \cdot d\tau. \quad (5)$$

The needed BG drop, $\Delta BG_{needed}$, must be calculated based on the target blood glucose value at $T=T_C+T_M$, or $BGT_{NI}$. Combining the results of (1), (2) and (5), and assuming that $BG_{pb}=0$, i.e., assuming that no insulin was administered during the interval $[T_C-T_M, T_C]$, the equation for computing a correction bolus amount, CB, to be administered at or near the current time $T=T_C$ and when the time duration, $T_M$, spans the current time interval and next time interval, which begins at time $T=T_{BNI}$, is thus given by:

$$CB = (BGM - BGT_{NI}) \bigg/ \left[ \left( IS_{CI} * \int_0^{T_{BNI}-T_C} h(\tau) d\tau \right) + \left( IS_{NI} * \int_{T_{BNI}-T_C}^{T_M} h(\tau) d\tau \right) \right]. \quad (6)$$

Solving (6) for the integrals yields the equation:

$$CB = (BGM - BGT_{NI})/\{[IS_{CI}*(h(T_{BNI}-T_C)-h(0))] + [IS_{NI}*(h(T_M)-h(T_{BNI}-T_C))]\} \quad (7),$$

wherein the quantity $(h(T_{BNI}-T_C)-h(0))$ corresponds to the fraction or percentage, $P_{CI}$, of the insulin action of the bolus given at or near $T=T_C$ that will be spent or used to lower the measured blood glucose value, BGM, during the current time interval, and the quantity $(h(T_M)-h(T_{BNI}-T_C))$ corresponds to the fraction or percentage, $P_{NI}$, of the insulin action of the bolus given at or near $T=T_C$ that will be spent or used to lower the measured blood glucose value, BGM, during the next adjacent time interval. Substituting the insulin action percentage variables into equation (7) yields the equation:

$$CB = (BGM - BGT_{NI})/[(IS_{CI}*P_{CI})+(IS_{NI}*P_{NI})] \quad (8).$$

Referring again to FIG. 2, another numerical example will be used to illustrate the effect of equation (8) on the blood glucose measurement value 58. Assume that the measured blood glucose value, BGM, corresponding to point 58, is again 200 mg/dl, the target blood glucose value during the current interval, $BGT_{CI}$, is again 120 mg/dl, the insulin sensitivity during the current interval, $IS_{CI}$, is again 30 mg/dl/IU, the target blood glucose value during the next adjacent time interval, $BGT_{NI}$, is again 150 mg/dl and the insulin sensitivity during the next adjacent time interval, $IS_{NI}$, is again 40 mg/dl/IU. Also assume that at $T=T_{BNI}$, 40% of the insulin action of an insulin bolus given at or near $T=T_C$ (corresponding to point 58) will have been spent to lower the glucose level during the current time interval. This leaves 1−0.4=60% of the insulin action of the insulin bolus given at or near $T=T_C$ to be spent lowering the glucose level during the next adjacent time interval. According to equation (8) then, the correction bolus, CB, that should be administered at or near $T_C$ (corresponding to point 58) is CB=(200 mg/dl−50 mg/dl)/[(30 mg/dl/IU*0.4)+(40 mg/dl/IU*0.6)]=1.388 IU, or approximately 1.4 IU. With an insulin sensitivity during the next adjacent time interval of 40 mg/dl, administering 1.4 IU of insulin at time $T=T_C$ (corresponding to point 58) results in a decrease 64 in blood glucose of [(30 mg/dl)*(1.4 IU)*0.4]+[(40 mg/dl)*(1.4 IU)*0.6]=50.4 mg/dl, corresponding to a decrease in blood glucose from 200 mg/dl at point 58 to a final glucose level in the next adjacent time interval equal to the target glucose level ($BGT_{NI}$) 52.

Figure 3:
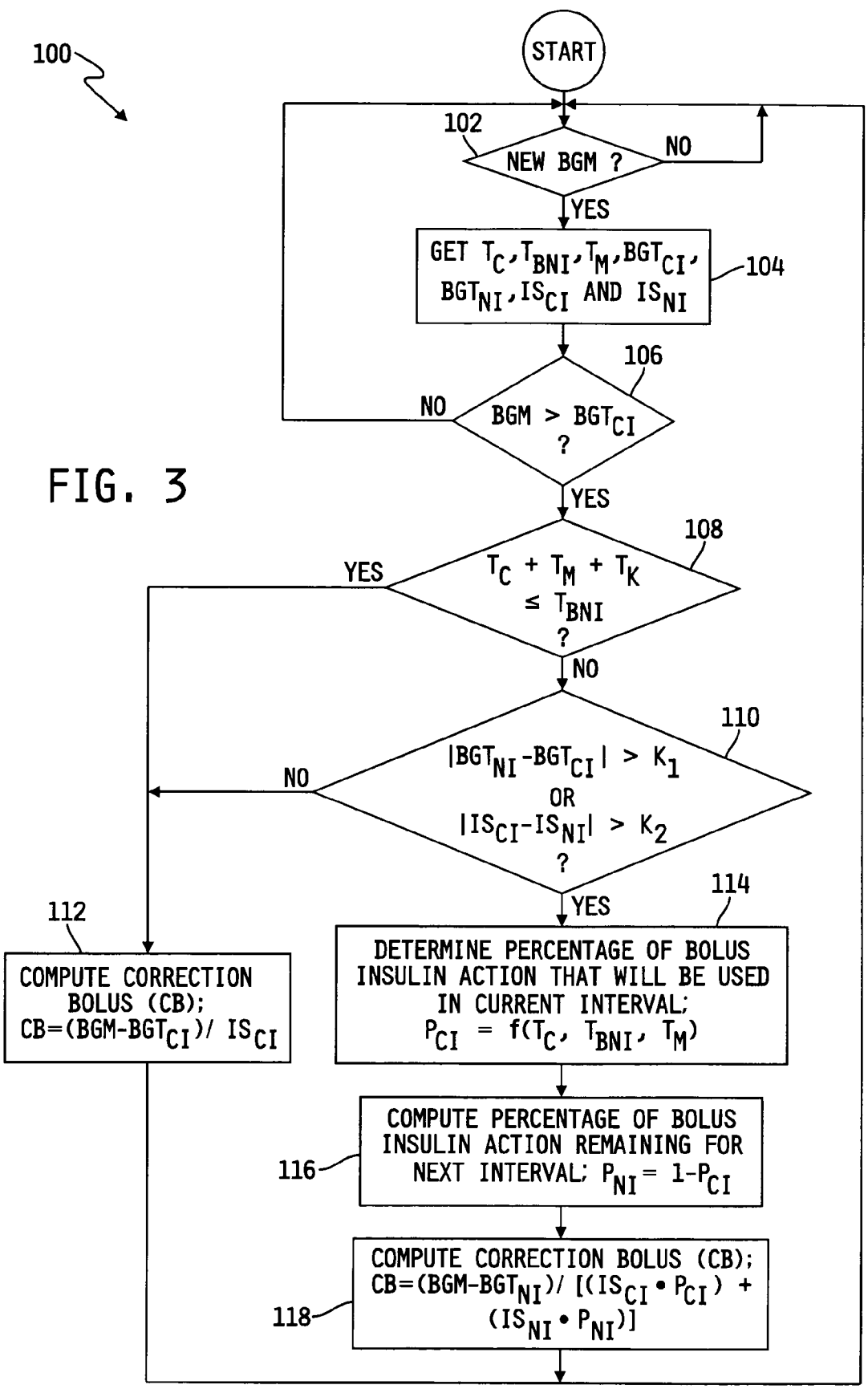
FIG. 3 is a flowchart of one illustrative embodiment of an insulin bolus recommendation software algorithm, executable by the system of FIG. 1, for determining and recommending insulin bolus quantities.

Referring now to FIG. 3, a flowchart is shown of one illustrative embodiment of a software algorithm 100 for determining recommended insulin bolus quantities under the various conditions presented by the foregoing examples. The insulin bolus recommendation software algorithm 100 of FIG. 3 will be described as being implemented with the insulin bolus recommendation unit 12 and executed by the control circuit 14, wherein the insulin bolus recommendation unit 12 is provided in the form of a conventional PDA or a hand-held, application-specific insulin bolus recommendation unit, although those skilled in the art will recognize that the algorithm 100 may alternatively be implemented with the bolus recommendation unit 12 and/or bolus recommendation unit 30 provided in any one or more of the physical forms described hereinabove.

In the illustrated embodiment, the algorithm 100 begins at step 102 where the control circuit 14 is operable to determine whether a new measured glucose value, BGM, is available. The algorithm 100, in the exemplary embodiment, presumes that glucose measurements taken at any current time, $T_C$, will be entered into, or otherwise be obtained, by the system 10 at or near the time $T_C$. Until a new glucose value, BGM, is received, the control circuit 14 will continue to loop back to the start of step 102. Otherwise when a new glucose measurement, BGM, becomes available, algorithm execution advances to step 104 where the control circuit is operable to obtain the necessary parameters relating to the current and next adjacent time intervals. In one embodiment, the necessary parameters are stored in the memory unit 20 and/or within the executable memory of the control circuit 14, and the control circuit 14 is operable to execute step 104 by retrieving these parameters from the memory unit 20 and/or from the executable memory of the control circuit 14. Alternatively, the necessary parameters may be entered into or otherwise provided to the system 10 using any one or more of the components described hereinabove with respect to FIG. 1. In any case, the necessary parameters obtained at step 104 in the exemplary embodiment include the current time value, $T_C$, the beginning time value of the next adjacent time interval, $T_{BNI}$, the time duration, $T_M$, of the glucose lowering action of the insulin bolus to possibly be administered at or near $T_C$, the glucose measurement value, BGM, the glucose target of the current time interval, $BGT_{CI}$, the glucose target of the next adjacent time interval, $BGT_{NI}$, the insulin sensitivity of the current time interval, $IS_{CI}$, and the insulin sensitivity of the next adjacent time interval, $IS_{NI}$.

Following step 104, the control circuit 14 is operable at step 106 to compare the measured glucose value, BGM, to the glucose target value of the current time interval, $BGT_{CI}$. If BGM does not exceed $BGT_{CI}$, execution of the algorithm 100 loops back to the beginning of step 102, otherwise the algorithm execution advances to step 108. Thus, the algorithm 100 does not advance past step 106 unless and until a new glucose measurement, BGM, is available and BGM exceeds $BGT_{CI}$. It will be understood that the algorithm 100 may be incorporated into another insulin bolus recommendation algorithm that is operable to execute steps 102 and 106. In such cases, the algorithm 100 may be modified to be accommodated by such an insulin bolus recommendation algorithm by omitting steps 102 and 106.

At step 108, the control circuit 14 is operable to compare a sum of $T_C$, $T_M$ and a constant time value, $T_K$, to the beginning time of the next adjacent time interval, $T_{BNI}$. If this sum is greater than $T_{BNI}$, algorithm execution advances to step 110. Otherwise, if this sum is less than or equal to $T_{BNI}$, algorithm execution advances to step 112. In one embodiment, $T_K$ is zero, and the sum of $T_C$ and $T_M$ represents the time value, relative to the current and next adjacent time intervals, that the insulin activity of a bolus, if administered at the current time, $T_C$, would be complete. Thus, if the sum of $T_C$ and $T_M$ is less than or equal to $T_{BNI}$, this indicates that $T_C$ is early enough in the current time interval that the time duration, $T_M$, of the glucose lowering action of an insulin bolus administered at time $T_C$ is confined to the current time interval. In this case, the computation of an accurate value of a correction bolus, CB, may be accomplished using the conventional equation (1). On the other hand, if the sum of $T_C$ and $T_M$ exceeds $T_{BNI}$, this indicates that $T_C$ is late enough in the current time interval that the time duration, $T_M$, of the glucose lowering action of an insulin bolus administered at time $T_C$ spans the current and the next adjacent time intervals. In this case, the computation of an accurate value of a correction bolus, CB, must be accomplished using the correction bolus equation (7) or (8) as described hereinabove. Embodiments of the algorithm 100 are contemplated in which the control circuit 14 is operable to compute a correction bolus, CB, according to equation (7) or (8) only if the time duration, $T_M$, of the glucose lowering action of the correction bolus to be administered at time $T_C$ extends into the next adjacent time interval by a predefined time amount. In such embodiments, the time constant $T_K$ will not be zero, but will instead be some positive time value that ensures that the inequality of step 108 does not lead to step 110 unless $T_M$ extends into the next adjacent time interval by the predefined time amount. As one specific example, the predefined time amount may be 30% of $T_M$, although it will be understood that other values of the predefined time amount may be used.

In any case, if the control circuit 14 determines at step 108 that the time duration, $T_M$, of the glucose lowering action of the correction bolus to be administered at time $T_C$ extends sufficiently into the next adjacent time interval, algorithm execution advances to step 110 where the control circuit is operable to compare an absolute value of a difference between $BGT_{CI}$ and $BGT_{NI}$ with a constant, K1, and to compare an absolute value of a difference between $IS_{CI}$ and $IS_{NI}$ with another constant, K2. In one embodiment, K1 and K2 are both zero, and the absolute values of the differences yield zero only if the target glucose and insulin sensitivity values do not change between the current and next adjacent time intervals. In this case, the computation of an accurate value of a correction bolus, CB, may be accomplished using the conventional equation (1). On the other hand, if either one or both of the target glucose or the insulin sensitivity values change between the current and next adjacent time intervals, the computation of an accurate value of a correction bolus, CB, must be accomplished using the correction bolus equation (7) or (8) as described hereinabove. Embodiments of the algorithm 100 are contemplated in which the constant values K1 and K2 are set at some positive constant values to thereby require the target glucose and/or the insulin sensitivity values to change by more than predefines amounts before computing the correction bolus, CB, according to equation (7) or (8). As one specific example, K1 and K2 may both be 5, although it will be understood that other values of K1 and K2 may be used wherein K1 may or may not be equal to K2.

In any case, if the time duration, $T_M$, of the glucose lowering action of an insulin bolus to be administered at time $T_C$ will be confined to the current time interval or at least not extend sufficiently into the next adjacent time interval, and neither of the glucose target value nor the insulin sensitivity value has changes significantly between the current and next adjacent time intervals, the control circuit 14 is operable at step 112 to compute the correction bolus, CB, according to equation (1) such that $CB=(BGM-BGT_{CI})/IS_{CI}$. If, on the other hand, the time duration, $T_M$, extends sufficiently into the next available time interval, or either one or both of the glucose target value and the insulin sensitivity value change significantly between the current and next available time intervals, the control circuit 14 is operable at step 114 to determine the fraction or percentage, $P_{CI}$, of bolus insulin action that will be used or spent lowering the glucose level in the current time interval.

In the illustrated embodiment, the control circuit 14 is operable to determine this fraction or percentage as a function of the current time, $T_C$, the beginning time of the next adjacent time interval, $T_{BNI}$, and the time duration, $T_M$, of the glucose lowering action of the correction bolus that will be administered at or near $T_C$. This function may be stored in the memory unit 20 in the form of one or more tables, graphs, charts, equations or the like, and in one specific embodiment this function is stored in the memory unit 20 in the form of a two-dimensional look up table. In this embodiment, the look up table has as one table axis time values corresponding to the difference between $T_{BNI}$ values and $T_C$ values and another table axis time duration values, $T_M$. The table is populated, in this embodiment, with percentage values, corresponding to percentages of bolus insulin action that will be used or spent lowering the glucose level in the current time interval, as functions of $T_M$ values and of time difference values, corresponding to $T_{BNI}-T_C$. Thereafter at step 116, the control circuit 14 is operable to determine the fraction or percentage, $P_{NI}$, of bolus insulin action that will be used or spent lowering the glucose level in the next adjacent time interval by subtracting the percentage, $P_{CI}$, determined at step 114, with respect to the current time interval, from 100%.

Those skilled in the art will recognize that the steps 114 and 116 may alternatively be modified so that the control circuit 114 is operable to compute the fraction or percentage, $P_{NI}$, of bolus insulin action that will be used or spent lowering the glucose level in the next adjacent time interval as a function of $T_C$, $T_{BNI}$ and $T_M$ using any of the techniques described hereinabove with respect to step 114, and to then determine the fraction or percentage, $P_{CI}$, of bolus insulin action that will be used or spent lowering the glucose level in the current time interval by subtracting the percentage, $P_{NI}$, determined at step 114, with respect to the next adjacent time interval, from 100%. In any case, algorithm execution advances from step 116 to step 118 where the control circuit 14 is operable to compute the correction bolus quantity, CB, according to equation (7) such that $CB=(BGM-BGT_{NI})/[(IS_{CI}*P_{CI})+(IS_{NI}*P_{NI})]$. Algorithm execution loops back from either of steps 112 or 118 to the beginning of step 102.

The present disclosure contemplates that the time duration, $T_M$, of the glucose lowering action of the insulin bolus to be administered at or near $T_C$ may span one or more of the next adjacent time intervals. This may occur as a result of any combination of a sufficiently long time duration, $T_M$, sufficiently short durations of one or more of the current time interval and/or any series of next adjacent time intervals, the timing of the current time, $T_C$, relative to the current time interval, and the like. In any case, equation (8) may be modified to account for the time duration, $T_M$, spanning any number, j, of next adjacent time intervals, wherein j may be any positive integer. One form of such an equation, based on equation (8), is the following:

$$CB = (BGM - BGT_{NI+j-1}) \bigg/ \sum_{n=-1}^{j-1} (IS_{NI+n} * P_{NI+n}), \quad (9)$$

where $IS_{NI+n}=IS_{CI}$ and $P_{NI+n}=P_{CI}$ when $n=-1$. According to equation (9), the blood glucose target value, BGT, used is that of the last, i.e., jth, one of the next adjacent time intervals, and the denominator of equation (9) represents the sum of IS and P products for all of the time intervals that $T_M$ spans, including the current time interval and all "j" of the next adjacent time intervals.

Figure 4A:
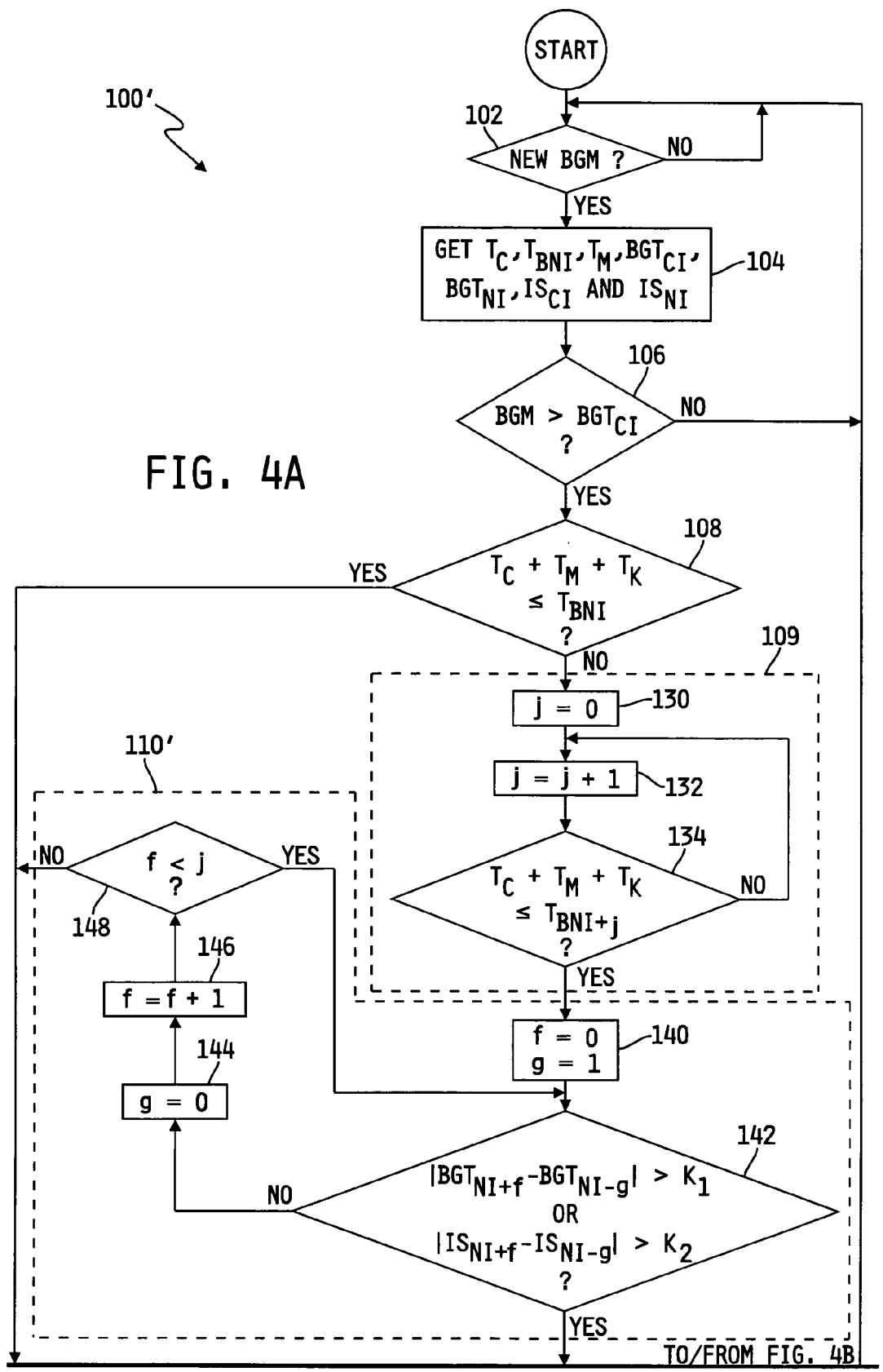
FIGS. 4A and 4B illustrate a flowchart of another illustrative embodiment of an insulin bolus recommendation software algorithm, executable by the system of FIG. 1, for determining and recommending insulin bolus quantities.
Figure 4B:
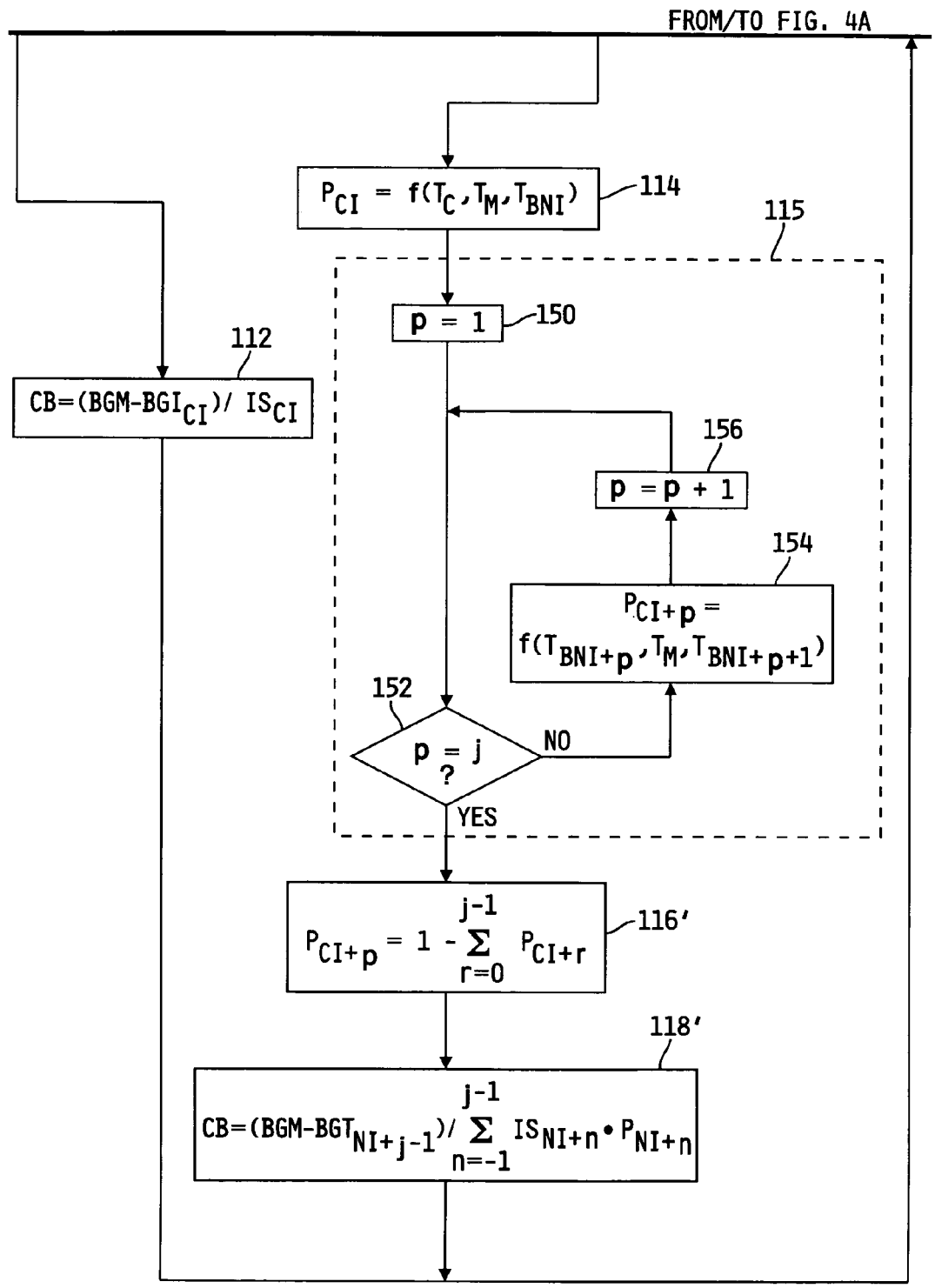

Referring now to FIGS. 4A and 4B, a flowchart is shown illustrating another illustrative embodiment of an insulin bolus recommendation software algorithm 100', executable by the system of FIG. 1, for determining and recommending insulin bolus quantities. The insulin bolus recommendation software algorithm 100' of FIGS. 4A and 4B will be described as being implemented with the insulin bolus recommendation unit 12 and executed by the control circuit 14, wherein the insulin bolus recommendation unit 12 is provided in the form of a conventional PDA or a hand-held, application-specific insulin bolus recommendation unit, although those skilled in the art will recognize that the algorithm 100' may alternatively be implemented with the bolus recommendation unit 12 and/or bolus recommendation unit 30 provided in any one or more of the physical forms described hereinabove. In any case, the algorithm 100' expands the concepts illustrated in FIG. 3 to embodiments wherein the time duration, $T_M$, of the glucose lowering action of the insulin bolus to be administered at or near time $T_C$ of the current interval may be confined to the current time interval, may span the current time interval and at least a portion of the next adjacent time interval, or may span the current time interval as well as a number, j, of next adjacent time intervals, where j may be any positive integer.

In the illustrated embodiment, the algorithm 100' includes many steps in common with the software algorithm 100 illustrated in FIG. 3, and like numbers are therefore used to identify like steps. The algorithm 100' is identical to the algorithm 100 in the execution of steps 102-108. Following the "YES" branch of step 108, however, the algorithm 100' includes an additional block 109 comprising the steps 130-134, for the purpose of determining the total number of next adjacent time intervals, j, following the current time interval that the time duration, $T_M$, of the glucose lowering action of the insulin bolus to be administered at or near the current time, $T_C$, spans. For example, at step 130, the control circuit 14 is operable to set a counter, j, of next adjacent time intervals that $T_M$ spans to zero. Thereafter at step 132, the control circuit 14 is operable to increment the counter, j, by one. Thereafter at step 134, the control circuit 14 is operable to determine if the sum of $T_C$, $T_M$ and $T_K$ is less than $T_{BNI+j}$, wherein each of the terms $T_C$, $T_M$ and $T_K$ is described hereinabove, and wherein the term $T_{BNI+j}$ represents the beginning time of the jth one of the next sequential, adjacent time intervals. As long as the sum of $T_C$, $T_M$ and $T_K$ is less than or equal to $T_{BNI+j}$, the algorithm 100' loops back to step 132. Thus, when the inequality of step 134 is true, the variable j represents the total number of next adjacent time intervals, beyond the current time interval, that is spanned by the time duration, $T_M$, of the glucose lowering action of the insulin bolus to be administered at or near the current time, $T_C$.

Step 110' of the algorithm 100' is similar to step 110 of the algorithm 100 of FIG. 3, but is modified to account for the possibility of $T_M$ spanning more than one of the next adjacent time intervals. Specifically, step 110 begins at step 140 where the control circuit 14 is operable to set a counter, f, equal to zero and a counter, g, equal to 1. Thereafter at step 142, the control circuit 14 is operable to determine whether the absolute value of the glucose difference $BGT_{NI+f}-BGT_{NI-g}$ is greater than a constant, K1, or whether the absolute value of the insulin sensitivity difference $IS_{NI+f}-IS_{NI-g}$ is greater than a constant, K2. When the counter, g, is equal to 1, $BGT_{NI-g}=BGT_{CI}$ and $IS_{NI-g}=IS_{CI}$. If neither of these inequalities is true, algorithm execution advances to steps 144 and 146 where the control circuit 14 is operable to set the counter, g, equal to zero and to increment the counter, f, by one. Thereafter at step 148, the control circuit 14 is operable to compare the value of f with the total number, j, of next adjacent time intervals spanned by $T_M$. If f is less than j, this indicates that the time duration, $T_M$, spans at least the next f+1 adjacent time interval, and algorithm execution loops back to the beginning of step 142. If, on the other hand, f is equal to j at step 148, this indicates that all "j" of the next adjacent time intervals have been tested and that the two inequalities of step 142 have not been true for any of the "j" next adjacent time intervals. This means that neither the glucose target, BGT, nor the insulin sensitivity, IS, changes enough between the current time interval and any of the next j time intervals to warrant computation of the correction bolus using equation (9) above, and instead the "NO" branch of step 148 advances to step 112, which is identical to step 112 of the algorithm 100 of FIG. 3, to compute the correction bolus, CB, according to the conventional equation (1).

If at any time during the execution of the loop defined by steps 142-148 either of the inequalities of step 142 are satisfied, this indicates that either the glucose target, BGT, or the insulin sensitivity, IS, changed sufficiently enough between the current time interval and any of the next j time intervals to warrant computation of the correction bolus using equation (9) above. Execution of the algorithm 100' thus advances from the "YES" branch of step 142 to step 114, which is identical to step 114 of the algorithm 100 of FIG. 3, and which computes the percentage, $P_{CI}$, of the insulin action of the insulin bolus to be administered at time $T_C$ that will be spent lowering the glucose level during the current time interval. Following step 114, execution of the algorithm 100' advances to an additional step 115 comprising the steps 150-156, for the purpose of determining a percentage, P, of the insulin action of the insulin bolus to be administered at time $T_C$ that will be spent lowering the glucose level during each of the next "j" adjacent time intervals. For example, at step 150, the control circuit 14 is operable to set a counter, p, equal to one. Thereafter at step 152, the control circuit 14 is operable to determine whether the counter value, p, is equal to the number, j, of next adjacent time intervals that $T_M$ spans. If not, algorithm execution advances to step 154 where the control circuit 14 is operable to compute the percentage, $P_{CI+p}$, of the insulin action of the bolus to be administered at $T_C$ that will be spent to lower the glucose level during the pth one of the next adjacent time intervals, as a function of $T_{BNI+p}$, $T_M$ and $T_{BNI+p+1}$ using any of the techniques described hereinabove with respect to the computation of $P_{CI}$. Thereafter at step 156, the control circuit 14 is operable to increment the counter value, p, by one, and from step 156 algorithm execution loops back to the beginning of step 152. Step 115, comprising steps 150-156, is thus operable to compute the percentages of the insulin action of the bolus to be administered at $T_C$ that will be spent to lower the glucose level during all but the last one of the next adjacent time intervals that $T_M$ spans.

From the "Yes" branch of step 152, algorithm execution advances to step 116' which is a modified version of step 116 of FIG. 3 in that the control circuit 14 is operable at step 116' to compute the percentage, $P_{CI+p}$, of the insulin action of the bolus to be administered at $T_C$ that will be spent to lower the glucose level during the last one of the next adjacent time intervals that $T_M$ spans, according to the equation $$P_{CI} + p = 1 - \sum_{r=o}^{j-1} P_{CI+r}.$$

From step 116', algorithm execution advances to step 118' which is a modified version of step 118 of FIG. 3 in that the control circuit 14 is operable at step 118' to compute the correction bolus, CB, according to equation (9), i.e., $$CB = (BGM - BGT_{NI+j-1}) \bigg/ \sum_{n=-1}^{j-1} (IS_{NI+n} * P_{NI+n}).$$

Algorithm execution loops from either of steps 112 and 118' back to step 102.

The present disclosure contemplates that either or both of the target glucose value, BGT, and the insulin sensitivity value, IS, may vary as a function of time during any one or more of the time intervals. In such a case, equation (6) may be modified to account for the time duration, $T_M$, spanning any number, j, of next adjacent time intervals, wherein j may be any positive integer, and to account for either or both the glucose target and the insulin sensitivity values being time dependent. One form of such an equation, based on equation (6), is the following:

$$CB = (BGM - BGT(T_C + T_M)) \bigg/ \quad (10)$$

$$\left( \int_0^{T_{BNI}-T_C} h(\tau) \cdot IS(T_C + \tau) d\tau + \int_{t_{BNI}-T_C}^{T_{BNI+1}} h(\tau) \cdot IS(T_C + \tau) d\tau + \right.$$

$$\left. \ldots + \int_{T_{BNI+j}}^{T_M} h(\tau) \cdot IS(T_C + \tau) d\tau \right),$$

where $BGT(T_C+T_M)$ represents the glucose target value at the time $T_C+T_M$. In such embodiments, a modified version of the algorithm 100' of FIGS. 4A and 4B may be used to compute CB according to equation (10), wherein steps 108 and 110' would be omitted, step 114 would be modified to compute the first integral term, $$\int_0^{T_{BNI}-T_C} h(\tau) \cdot IS(T_C + \tau) d\tau,$$

step 154 would be modified to compute the middle integral terms, e.g., $$\int_{T_{BNI}-T_C}^{T_{BNIH}-T_C} h(\tau) \cdot IS(T_C + \tau) d\tau,$$

and step 116' would be modified to compute the last integral term $$\int_{T_{BNI-j}-T_C}^{T_M} h(\tau) \cdot IS(T_C + \tau) d\tau.$$

Step 118 would also be modified to compute CB according to equation (10).

where $IS_{NI+n}=IS_{CI}$ and $P_{NI+n}=P_{CI}$ when n=-1. According to equation (9), the blood glucose target value, BGT, used is that of the last, i.e., jth, one of the next adjacent time intervals, and the denominator of equation (9) represents the sum of IS and P products for all of the time intervals that $T_M$ spans, including the current time interval and all "j" of the next adjacent time intervals.

The present disclosure contemplates embodiments of the diabetes care system wherein the extended time period, e.g., one or more days, is not partitioned into a number of time intervals, but wherein continuous functions of the glucose target, BGT and the insulin sensitivity, IS, are defined for the entire extended time period. In such cases, the correction bolus equation may take the form:

$$CB = (BGM - BGT(T_C + T_M)) \bigg/ \int_0^{T_M} h(\tau) \cdot IS(T_C + \tau) d\tau. \quad (11)$$

In such embodiments, another modified version of the algorithm 100' of FIGS. 4A and 4B may be used to compute CB according to equation (11), wherein steps 108, 109, 110', 114, 115 and 116' would be omitted, and step 118' would be modified to compute CB according to equation (11).

While the invention has been illustrated and described in detail in the foregoing drawings and description, the same is to be considered as illustrative and not restrictive in character, it being understood that only illustrative embodiments thereof have been shown and described and that all changes and modifications that come within the spirit of the invention are desired to be protected.

What is claimed is:

1. A method of computing a recommended insulin bolus quantity when a measured glucose value in a current time interval of a number of adjacent time intervals, each of the number of adjacent time intervals defining an associated target glucose value and an insulin sensitivity value, exceeds the target glucose value for the current time interval and when a time duration of glucose lowering action of the recommended insulin bolus quantity to be administered extends from the current time interval into a number of next adjacent time intervals, the method comprising the steps of:

determining with a processor a plurality of percentages each corresponding to a percentage of insulin action of the recommended bolus quantity that will be used lowering the glucose level during a respective one of the current time interval and each of the number of next adjacent time intervals, and computing with the processor the recommended bolus quantity as a function of the measured glucose value, the target blood glucose level for a last one of the number of next adjacent time intervals, the insulin sensitivities for the current and each of the number of next adjacent time intervals, and the plurality of percentages.

2. The method of claim 1 wherein the number of next adjacent time intervals is one, and wherein the step of determining with a processor a plurality of percentages includes:
determining with the processor a first percentage corresponding to a percentage of insulin action of the recommended bolus quantity that will be used lowering the glucose level during the current time interval,
determining with the processor a second percentage corresponding to a percentage of insulin action of the recommended bolus quantity that will be used lowering the glucose level during the next adjacent time interval,
and wherein the computing step includes computing the recommended bolus quantity as a function of the measured glucose value, the target blood glucose level for the next adjacent time interval, the insulin sensitivities for the current and next adjacent time intervals, and the first and second percentages.

3. The method of claim 2 wherein the step of determining a first percentage includes determining the first percentage as a function of at least a current time in the current time interval at which the measured bolus value was measured, a beginning time of the next adjacent time interval and the time duration of glucose lowering action of the subsequently administered recommended insulin bolus quantity.

4. The method of claim 3 further including the step of computing with the processor a current interval bolus activity time as a difference between the beginning time of the next adjacent time interval and the current time,
and wherein the step of determining a first percentage includes determining the first percentage as a function of the current interval bolus activity time and the time duration of glucose lowering action of the subsequently administered recommended insulin bolus quantity.

5. The method of claim 4 wherein the step of determining a first percentage includes extracting the first percentage value from a table populated with first percentage values as functions of current interval bolus activity time values and time duration values of glucose lowering action of the subsequently administered recommended insulin bolus quantity.

6. The method of claim 3 wherein the step of determining a second percentage includes computing the second percentage as a difference between one hundred percent and the first percentage.

7. The method of claim 2 wherein the step of determining a second percentage includes determining the second percentage as a function of at least a current time in the current time interval at which the measured bolus value was measured, a beginning time of the next adjacent time interval and the time duration of glucose lowering action of the subsequently administered recommended insulin bolus quantity.

8. The method of claim 7 further including the step of computing with the processor a next interval bolus activity time as a difference between the time duration of glucose lowering action of the subsequently administered recommended insulin bolus quantity and a current interval bolus activity time corresponding to a difference between the beginning time of the next adjacent time interval and the current time,
and wherein the step of determining a second percentage includes determining the second percentage as a function of the next interval bolus activity time and the time duration of glucose lowering action of the subsequently administered recommended insulin bolus quantity.

9. The method of claim 8 wherein the step of determining a second percentage includes extracting the second percentage value from a table populated with second percentage values as functions of next interval bolus activity time values and time duration values of glucose lowering action of the subsequently administered recommended insulin bolus quantity.

10. The method of claim 7 wherein the step of determining a first percentage includes computing the first percentage as a difference between one hundred percent and the second percentage.

11. The method of claim 2 further including the step of executing both determining steps and the computing step only if the time duration of glucose lowering action of the subsequently administered recommended insulin bolus quantity extends into the next adjacent time interval by a predefined time amount.

12. A method of computing a recommended insulin bolus quantity when a measured glucose value in a current time interval of a number of adjacent time intervals, each of the number of adjacent time intervals defining an associated target glucose value and an insulin sensitivity value, exceeds the target glucose value for the current time interval, the method comprising:
determining with a processor whether a time duration of glucose lowering action of the subsequently administered recommended insulin bolus quantity extends from the current time interval into at least a next adjacent time interval, and
computing with the processor the recommended bolus quantity as a function of the measured glucose value, the target glucose value for the current time interval and the insulin sensitivity value for the current time interval only if the time duration of glucose lowering action of the subsequently administered recommended insulin bolus quantity is confined to the current time interval.

13. The method of claim 12 further including the following steps if the time duration of the glucose lowering action of the subsequently administered recommended insulin bolus quantity extends from the current time interval into a number of the next adjacent time interval:
determining with the processor a plurality of percentages each corresponding to a percentage of insulin action of the recommended bolus quantity that will be used lowering the glucose level during a respective one of the current time interval and each of the number of next adjacent time intervals, and
computing with the processor the recommended bolus quantity as a function of the measured glucose value, the target blood glucose level for a last one of the number of next adjacent time intervals, the insulin sensitivities for the current and each of the number of next adjacent time intervals, and the plurality of percentages.

14. The method of claim 13 wherein the number of next adjacent time intervals is one,
and wherein the step of determining a plurality of percentages includes:
determining with the processor a first percentage corresponding to a percentage of insulin action of the recommended bolus quantity that will be used lowering the glucose level during the current time interval,
determining with the processor a second percentage corresponding to a percentage of insulin action of the recommended bolus quantity that will be used lowering the glucose level during the next adjacent time interval,
and wherein the computing step includes computing the recommended bolus quantity as a function of the measured glucose value, the target blood glucose level for the next adjacent time interval, the insulin sensitivities for the current and next adjacent time intervals, and the first and second percentages.

15. The method of claim 14 wherein the step of determining a first percentage includes determining the first percentage as a function of at least a current time in the current time interval at which the measured bolus value was measured, a beginning time of the next adjacent time interval and the time duration of glucose lowering action of the subsequently administered recommended insulin bolus quantity.

16. The method of claim 15 wherein the step of determining a second percentage includes computing the second percentage as a difference between one hundred percent and the first percentage.

17. The method of claim 14 wherein the step of determining a second percentage includes determining the second percentage as a function of at least a current time in the current time interval at which the measured bolus value was measured, a beginning time of the next adjacent time interval and the time duration of glucose lowering action of the subsequently administered recommended insulin bolus quantity.

18. The method of claim 17 wherein the step of determining a first percentage includes computing the first percentage as a difference between one hundred percent and the second percentage.

19. The method of claim 14 further including the step of executing the steps of determining the first and second percentages and the step of computing the recommended bolus quantity as a function of the measured glucose value, the target blood glucose level for the next adjacent time interval, the insulin sensitivities for the current and next adjacent time intervals, and the first and second percentages only if the time duration of glucose lowering action of the subsequently administered recommended insulin bolus quantity extends into the next adjacent time interval by a predefined time amount.

20. A method of computing a recommended insulin bolus quantity when a measured glucose value in a current time interval of a number of adjacent time intervals, each of the number of adjacent time intervals defining an associated target glucose value and an insulin sensitivity value, exceeds the target glucose value for the current time interval and when a time duration of glucose lowering action of the recommended insulin bolus quantity to be administered extends from the current time interval into the next adjacent time interval, the method comprising:
  determining with a processor a first difference as a difference between the target glucose value for the current time interval and the target glucose value for the next adjacent time interval,
  determining with the processor a second difference as a difference between the insulin sensitivity value for the current time interval and the insulin sensitivity value for the next adjacent time interval, and
  computing with the processor the recommended bolus quantity as a function of the measured glucose value, the target glucose value for the current time interval and the insulin sensitivity value for the current time interval only if the first difference is less than or equal to a first threshold value and the second difference is less than or equal to a second threshold value.

21. The method of claim 20 further including the following steps if either of the first difference exceeds the first threshold value and the second difference exceeds the second threshold value:
  determining with the processor a first percentage corresponding to a percentage of insulin action of the recommended bolus quantity that will be used lowering the glucose level during the current time interval,
  determining with the processor a second percentage corresponding to a percentage of insulin action of the recommended bolus quantity that will be used lowering the glucose level during the next adjacent time interval, and
  computing with the processor the recommended bolus quantity as a function of the measured glucose value, the target blood glucose level for the next adjacent time interval, the insulin sensitivities for the current and next adjacent time intervals, and the first and second percentages.

22. The method of claim 21 wherein the step of determining a first percentage includes determining the first percentage as a function of at least a current time in the current time interval at which the measured bolus value was measured, a beginning time of the next adjacent time interval and the time duration of glucose lowering action of the subsequently administered recommended insulin bolus quantity.

23. The method of claim 22 wherein the step of determining a second percentage includes computing the second percentage as a difference between one hundred percent and the first percentage.

24. The method of claim 21 wherein the step of determining a second percentage includes determining the second percentage as a function of at least a current time in the current time interval at which the measured bolus value was measured, a beginning time of the next adjacent time interval and the time duration of glucose lowering action of the subsequently administered recommended insulin bolus quantity.

25. The method of claim 24 wherein the step of determining a first percentage includes computing the first percentage as a difference between one hundred percent and the second percentage.

26. The method of claim 21 further including the step of executing the steps of determining the first and second percentages and the step of computing the recommended bolus quantity as a function of the measured glucose value, the target blood glucose level for the next adjacent time interval, the insulin sensitivities for the current and next adjacent time intervals, and the first and second percentages only if the time duration of glucose lowering action of the subsequently administered recommended insulin bolus quantity extends into the next adjacent time interval by a predefined time amount.

* * * * *